United States Patent [19]

Oishi et al.

[11] Patent Number: 5,145,780
[45] Date of Patent: Sep. 8, 1992

[54] **METHOD OF DECOMPOSING NUCLEIC ACIDS WITH A HEAT STABLE NUCLEASE FROM *TRICHODERMA* OR *FUSARIUM***

[75] Inventors: Kunio Oishi; Shuichi Aoi, both of Tokyo, Japan

[73] Assignee: Kabushikikaisha Kibun & Kabushikikaisha Kibun Fudokemifa, Tokyo, Japan

[21] Appl. No.: 807,816

[22] Filed: Dec. 16, 1991

Related U.S. Application Data

[63] Continuation of Ser. No. 382,589, Jul. 20, 1989, abandoned.

[30] Foreign Application Priority Data

Jan. 31, 1989 [JP] Japan .................................. 1-21865
Jan. 31, 1989 [JP] Japan .................................. 1-21866

[51] Int. Cl.$^5$ ...................... C12P 19/30; C12P 19/28; C12N 9/16; C12N 1/00
[52] U.S. Cl. ...................... 435/262; 435/85; 435/87; 435/196; 435/929; 435/945; 435/270; 435/89; 435/267
[58] Field of Search ............... 435/209, 929, 945, 196, 435/267, 85, 87, 89, 270, 262

[56] References Cited

U.S. PATENT DOCUMENTS

| | | |
|---|---|---|
| 3,966,543 | 6/1976 | Cayle et al. ............ 435/209 |
| 4,487,831 | 12/1984 | Day et al. .............. 435/209 |
| 4,562,150 | 12/1985 | Yamanobe et al. ........ 435/209 |
| 4,628,029 | 12/1986 | Eveleigh et al. ........ 435/209 |

OTHER PUBLICATIONS

Oleson et al, *Si Nuclease of Aspergillus ovyzae* . . . Archives of Biochem. & Biophys., vol. 211, No. 1, pp. 478–484, 1981.

Oleson et al, *Si Nuclease of Aspergillus ovyzae* . . . Archives of Biochem. & Biophys., vol. 204, No. 1 p. 361–370, 1980.

Advertisement from *Science*, graph cited for illustrative purposes.

*Primary Examiner*—David M. Naff
*Assistant Examiner*—Mike Meller
*Attorney, Agent, or Firm*—Nixon & Vanderhye

[57] ABSTRACT

An enzyme preparation is obtained containing a nuclease that is produced by a fungus such as *Trichoderma, Aspergillus* and *Fusarium* and which remains active even after heating at 100° C. for 30 minutes. This enzyme preparation may be effectively used when it is necessary to decompose nucleic acids at elevated temperature over a prolonged period.

4 Claims, 7 Drawing Sheets

20  30  40  45  50  60  70 °C

Fig. 7
A
0.6% AGAROSE
1.2% AGAROSE
0 3 5 10 15 30 45 60 (min)
Fig. 7
B

METHOD OF DECOMPOSING NUCLEIC ACIDS WITH A HEAT STABLE NUCLEASE FROM *TRICHODERMA* OR *FUSARIUM*

This is a continuation of application Ser. No. 07/382,589, filed Jul. 20, 1989, now abandoned.

BACKGROUND OF THE INVENTION

The present invention relates to an enzyme preparation comprised of highly heat-resistant nuclease active fractions present in the product of fungi. More specifically, the present invention relates to an enzyme preparation comprised of nuclease active fractions that will not lose their activity even after heating at 100° C. for 30 minutes.

Various enzyme preparations comprised of cellulase produced by fungi are commercially available, among which are Cellulase Onozuka ® (derived from Trichoderma and manufactured by Kinki Yakult Co., Ltd.), Cellulase AP ® (derived from Aspergillus and manufactured by Amano Seiyaku Co., Ltd.) and Toyo Cellulase ® (derived from Fusarium and manufactured by Toyo Jozo Co., Ltd.). These cellulose preparations are known to contain various enzymes that decompose polysaccharides or proteins. Some of these enzymes have already been isolated and their properties have been reviewed. Because of their nature, these cellulase-containing preparations are used extensively for decomposing polysaccharides and proteins. However, no attempt has been made to review the action these cellulase preparations and the products of fungi will exert on DNA. No knowledge has been obtained as to whether they have nuclease activity.

While a great number of enzymes have been known, most of them are labile to heat and their activity will decrease so greatly upon heating as to suffer a substantial loss in practical value. In particular, those enzymes which are capable of maintaining their activity even if they are heated at 100° C. for 30 minutes and longer are almost nil. A need has, therefore, arisen for the development of enzyme preparations that are capable of maintaining their activity even if they are exposed to prolonged heating at elevated temperatures.

SUMMARY OF THE INVENTION

One object of the present invention is to provide an enzyme preparation comprised of highly heat-resistant nuclease active fractions that occur in the products of fungi.

Another object of the present invention is to provide a nuclease enzyme preparation that has such high heat resistance that its enzymatic activity will not be lost upon heating at 100° C. for 30 minutes and longer.

The present invention has been accomplished on the basis of the finding by the present inventors of the fact that nuclease activity occurred in the products of fungi. Stated more specifically, the present invention has been accomplished on the basis of the first discovery by the present inventors of the fact that fungal products such as Cellulase Onozuka ® derived from Trichoderma, Cellulase AP ® derived from Aspergillus and Toyo Cellulase ® derived from Fusarium have nuclease activity (see Example 1 to be described hereinafter). In accordance with the present invention, nuclease active fractions are isolated from the product of fungi and used as the active ingredient of a nuclease enzyme preparation.

BRIEF DESCRIPTION OF THE DRAWINGS

FIGS. 7a and 7b show the relationship between time and the decomposition of λDNA by nuclease active fractions.

DETAILED DESCRIPTION OF THE INVENTION

Figure 1A:
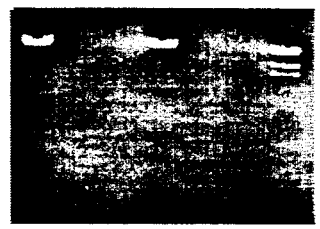
FIGS. 1a, 1b and 1c show the λDNA decomposing activity of a cellulase enzyme preparation.

The nuclease active fractions of the present invention may be obtained from the products of fungi by the following methods but it should be understood that the nuclease active fractions that can be used in the present invention are not limited to those which are obtained by these methods. According to one method for obtaining the nuclease active fractions of the present invention, a solution (pH 7.0) of a cellulase preparation derived from fungi such as Cellulase Onozuka ®, Cellulase AP ® or Toyo Cellulase ® is heated at 80° C. for 10 minutes and after removing the resulting insoluble product of heat denaturation, the solution is charged in a DEAE-Sephadex ® chromatographic column, which is then eluted with 0.5M NaCl (see Examples 2-4). Alternatively, a solution of cellulase preparation not heated to 80° C. may be directly subjected to DEAE-Sephadex ® column chromatography and the fractions not adsorbed at pH of 7.0 are recovered (see Examples 5-7). If desired, a fungus of a genus such as Trichoderma, Aspergillus or Fusarium is cultured in a medium such as a potato dextrose medium or Sabouraud's agar medium, ethanol is added to the culture obtained, the supernatant is separated, and the separated supernatant is treated by one of the methods described above to obtain nuclease active fractions.

Investigations of nuclease activity against λDNA showed that the activity was detected in the fractions of the present invention obtained by the methods described above, but not at all in other fractions (see Example 8). This made it clear that the nuclease activity found in the product of fungi was due solely to the fractions of the present invention. It is therefore anticipated that the concentrate of such active fractions that are selectively recovered from the product of fungi or cellulase enzyme preparations derived therefrom will have higher levels of nuclease activity than that inherently present in the products of fungi or enzyme preparations derived therefrom. Furthermore, said concentrate has the potential to exhibit higher selectivity.

The active fractions of the present invention have a very high level of heat resistance (see Examples 9 and 10). The active fractions of the present invention exhibit nuclease activity in a high temperature range of 60°–100° C. and particularly high activities are exhibited by active fractions derived from Aspergillus or Fusarium. The active fractions of the present invention have a marked advantage over the conventional enzymes in that they will not lose their activity even if they are heated at 100° C. for 30 minutes. Active fractions derived from Trichoderma retained their activity even after heating at 100° C. for 45 minutes (see Example 10). The enzyme preparation of the present invention which is comprised of such highly heat-resistant fractions will be effectively used in various applications such as where it is necessary to decompose nucleic acids at high temperatures. An optimum temperature for the decomposition of λDNA is 45° C. for active fractions derived from Trichorderma (see Example 11).

The nuclease active fractions of the present invention have another characteristic feature in that they are capable of yielding DNA decomposition products of uniform length. When DNA is decomposed with an enzyme, decomposition products of various lengths will normally result. However, if one uses the nuclease active fractions of the present invention, he can obtain decomposition products of a fairly uniform length. For instance, if active fractions of the present invention are allowed to act on λDNA, the lengths of decomposition products will become substantially uniform in 30–45 minutes after the reaction is started (see Example 12).

Another advantage of the nuclease active fractions of the present invention is that they have a sufficiently low level of substrate specificity to be used extensively in decomposing various kinds of nucleic acids. For example, these fractions exhibit satisfactory activity against a broad spectrum of substrates including λDNA, heat-denatured λDNA, bovine thymus DNA, heat-denatured bovine thymus DNA, herring sperm DNA, heat-denatured herring sperm DNA, M13 DNA, yeast RNA and calf liver DNA (see Example 13).

The processes for preparing the nuclease active fractions of the present invention, as well as their activities are described below in greater detail.

EXAMPLE 1

The nuclease activities of cellulase enzyme preparations were investigated by the following methods.

Figure 1B:
Figure 1C:

Solutions having an enzyme concentration of 20 mg/ml (0.05M phosphate buffer, pH 7.0) were prepared from each of the following five cellulase preparations: Cellulase Onozuka ® (product of Kinki Yakult Co., Ltd.; sample 1), Dorimelase ® (product of Kyowa Hakko Kogyo Co., Ltd.; sample 2), Nagase ® (product of Nagase & Company, Ltd.; sample 3), Toyo Cellulase ® (product of Toyo Jozo Co., Ltd.; sample 4), and Cellulase AP ® (product of Amano Seiyaku Co., Ltd.; sample 5). These solutions were allowed to act on λDNA for 1 hour at 35° C., 45° C. or 55° C., and the mixture were subjected to electrophoresis through agarose gel at a current of 38 mA for 1 hour. The resulting profiles are shown in FIG. 1, in which (a), (b) and (c) refer to the profiles obtained at 35° C., 45° C. and 55° C., respectively. Symbols A to G respectively correspond to the following: λDNA, sample 1, sample 2, sample 3, sample 4, sample 5 and the marker prepared by treating λDNA with HindIII.

EXAMPLE 2

Nuclease active fractions of the present invention were obtained by the following method.

A 2% solution of Cellulase Onozuka 3S ® (product of Kinki Yakult Co., Ltd.) whose pH was held at 7.0 with 0.05M phosphate buffer was heated at 80° C. for 10 minutes. The insoluble product of heat denaturation that formed upon heating was removed by centrifugation and the supernatant was charged into a DEAE-Sephadex ® A-50 chromatographic column and fractions obtained by elution with 0.5M NaCl were recovered.

EXAMPLE 3

Nuclease active fractions were obtained by repeating the procedures of Example 2 except that Cellulase Onozuka ® (product of Kinki Yakult Co., Ltd.) was replaced by Cellulase AP ® (product of Amano Seiyaku Co., Ltd.)

EXAMPLE 4

Nuclease active fractions were obtained by repeating the procedures of Example 2 except that Cellulase Onozuka ® (product of Kinki Yakult Co., Ltd.) was replaced by Toyo Cellulase ® (product of Toyo Jozo Co., Ltd.)

EXAMPLE 5

Nuclease active fractions of the present invention were obtained by the following method.

A 2% solution of Cellulase Onozuka 3S ® (product of Kinki Yakult Co., Ltd.) having its pH held at 7.0 with 0.05M phosphate buffer was prepared. This solution was loaded on a DEAE-Sephadex ® A-50 column and unabsorbed fractions were recovered.

EXAMPLE 6

Nuclease active fractions were obtained by repeating the procedures of Example 5 except that Cellulase Onozuka ® (product of Kinki Yakult Co., Ltd.) was replaced by Cellulase AP ® (product of Amano Seiyaku Co., Ltd.)

Example 7

Nuclease active fractions were obtained by repeating the procedures of Example 5 except that Cellulase Onozuka ® (product of Kinki Yakult Co., Ltd.) was replaced by Toyo Cellulase ® (product of Toyo Jozo Co., Ltd.)

EXAMPLE 8

The nuclease activities of fractions prepared in accordance with the present invention were compared with those of other fractions.

A 2% solution of Cellulase Onozuka 3S ® (product of Kinki Yakult Co., Ltd.) having its pH held at 7.0 with 0.05M phosphate buffer was prepared. This solution was loaded on a DEAE-Sephadex ® A-50 column and fractions unabsorbed at pH of 7.0 (the first group of fractions) were obtained. Thereafter, with the concentration of NaCl being gradually increased from 0 to 2 moles, the second, third and fourth group of fractions were eluted. The individual fractions were separated by observing the optical density at 280 nm (see FIG. 2).

The activity for decomposition of λDNA was investigated by observing the profiles of electrophoresis through agarose gel. The results were as shown in FIG. 3 for the first group of fractions, and in the upper part of FIG. 2 for the second, third and fourth group of fractions. The profile of λDNA per se was as shown at the left end of FIG. 3.

Figure 2:
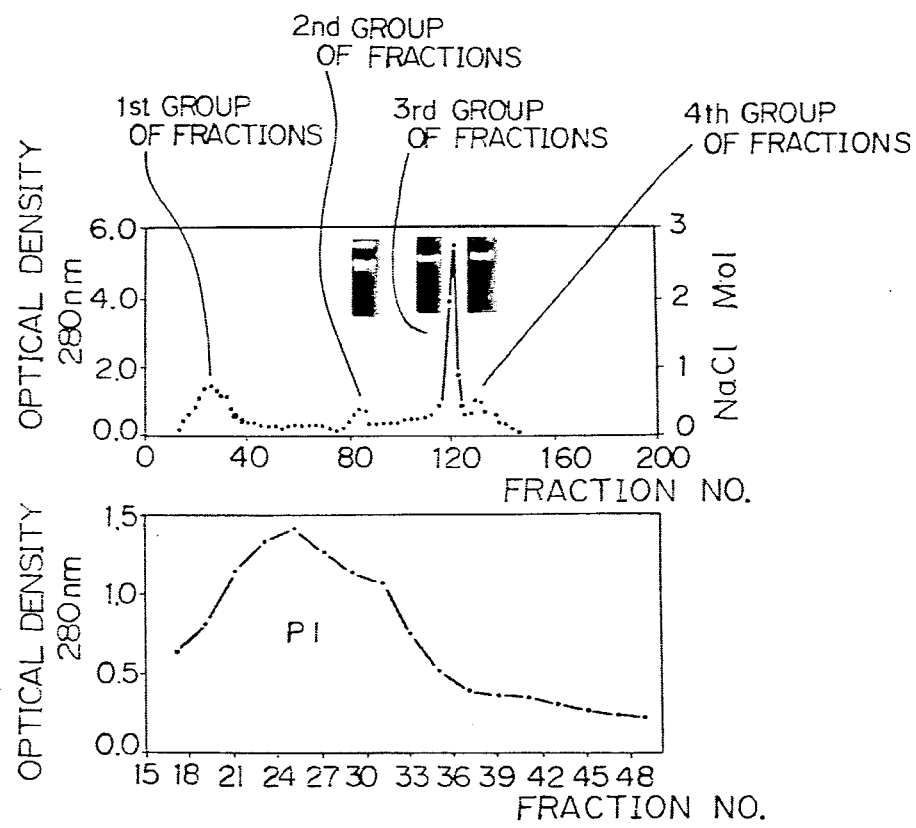
FIG. 2 shows the relationship between fractions in a DEAE-Sephadex ® column chromatogram and optical density at 280 nm.
Figure 3:
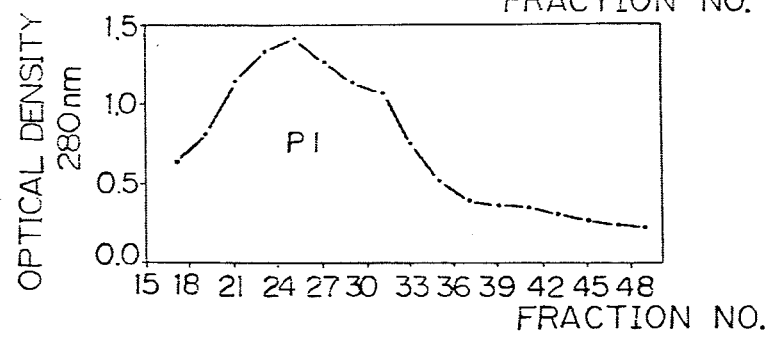
FIGS. 3a and 3b the λDNA decomposing activities of various nuclease active fractions.
Figure 3:

As is clear from FIGS. 2 and 3, a peak of decomposition activity centering at fraction No. 31 was observed for the first group of fractions. However, no decomposition activity was observed for the second, third and fourth group of fractions.

EXAMPLE 9

The heat resistance of active fractions prepared in accordance with the present invention was examined by the following method.

The active fractions obtained in Examples 5, 6 and 7 were allowed to act on λDNA after their enzyme concentration was adjusted to 20 mg/ml.

Condition 1: reaction temperature, 60° C.; reaction time, 10 minutes
Condition 2: reaction temperature, 70° C.; reaction time, 10 minutes
Condition 3: reaction temperature, 80° C.; reaction time, 10 minutes
Condition 4: reaction temperature, 100° C.; reaction time, 10 minutes
Condition 5: reaction temperature, 100° C.; reaction time, 30 minutes
Condition 6: reaction temperature, 100° C.; reaction time, 60 minutes.

Figure 4A:
FIGS. 4a, 4b and 4c show the changes in nuclease activity that accompany treatments at elevated temperatures.
Figure 4B:
Figure 4C:

The mixtures were subjected to electrophoresis at a current of 38 mA through agarose gel for 1 hour. The resulting profiles are shown in FIG. 4, in which (a), (b) and (c) refer to the profiles for the active fractions obtained in Example 5, 6 and 7, respectively. Symbols A–I denote the following: λDNA left intact (A); λDNA treated with the reaction solution from which active fractions were yet to be isolated (B); λDNA treated with active fractions under condition 1 (C); λDNA treated with active fractions under condition 2 (D); λDNA treated with active fractions under condition 3 (E); λDNA treated with active fractions under condition 4 (F); λDNA treated with active fractions under condition 5 (G); λDNA treated with active fractions under condition 6 (H); and λDNA treated with HindIII (I).

EXAMPLE 10

The heat resistance of active fractions prepared in accordance with the present invention was investigated by the following method.

Figure 5:
FIG. 5 shows the heat resistance of nuclease active fractions and the profile of change in their activity with temperature.

The first group of fractions obtained in Example 5 in accordance with the present invention were heated at 100° C. for different periods of time, i.e. 0, 10, 20, 30, 45 and 60 minutes, and their activities in decomposing λDNA were investigated in terms of profiles of electrophoresis through agarose gel (see the upper part of FIG. 5). Compared to 0-minute heating, 10-, 20- and 30-minute heatings caused a gradual decrease in activity but the fractions yet retained substantially high levels of activity. They were considerably attenuated by heating for 45 minutes but they still had detectable levels of activity.

EXAMPLE 11

The relationship between temperature and the activity of active fractions prepared in accordance with the present invention was investigated.

The active fractions were heated for 10 minutes at varying temperatures of 0°, 40°, 50°, 60°, 70°, 80°, 90° and 100° C. and their activities in decomposing λDNA were investigated in terms of profiles of electrophoresis through agarose gel (see the lower portion of FIG. 5). Between 0° and 50° C., no substantial difference in activity was observed, but the activities of the fractions decreased at 60° C. and were not detectable at all at 70° C. Nevertheless, uniform activities were observed again at 80°–100° C.

Figure 6:
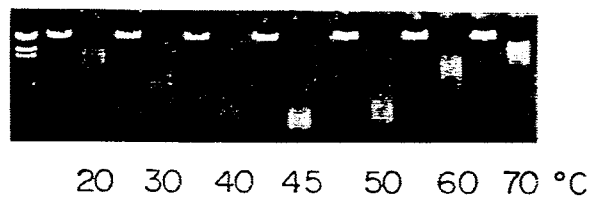
FIG. 6 shows the profile of change in the activity of nuclease active fractions with temperature.

Detailed activity investigations conducted at respective temperatures of 20°, 30°, 40°, 45°, 50°, 60° and 70° C. showed that an optimal temperature for the first group of fractions was 45° C. (FIG. 6).

EXAMPLE 12

The relationship between time and the decomposition of λDNA by active fractions prepared in accordance with the present invention was investigated.

To the first group of fractions obtained in Example 5, λDNA was added and the mixtures were subjected to electrophoresis through agarose gel for 0, 3, 5, 10, 15, 30, 45 and 60 minutes. The resulting electrophoretic profiles are shown in FIG. 7, from which one can see that the lengths of decomposition products became uniform 30–45 minutes after the addition of λDNA. Their length was calculated to be 500 bp for 0.6% agarose and 400 bp for 1.2% agarose.

EXAMPLE 13

The substrate specificity of active fractions prepared in accordance with the present invention was investigated.

Figure 8:
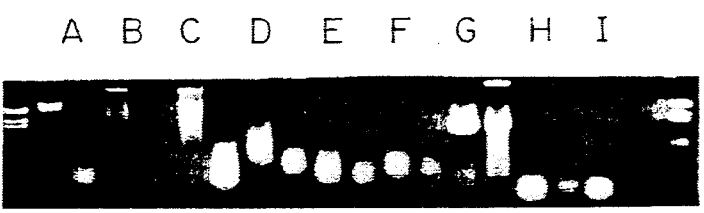
FIG. 8 shows the substrate specificity of nuclease active fractions.

The second group of fractions obtained in Example 5 were reacted with λDNA (A), heat-denatured λDNA (B), bovine thymus DNA (C), heat-denatured bovine thymus DNA (D), herring sperm DNA (E), heat-denatured herring sperm DNA (F), M13 DNA (G), yeast RNA (H), and calf liver DNA (I) and the mixtures were subjected to electrophoresis through agarose gel. The resulting electrophoretic profiles are shown in FIG. 8, from which one can see that each of the substrates tested decomposed, indicating the low substrate specificity of the active fractions prepared in accordance with the present invention.

What is claimed is:

1. A method of decomposing nucleic acids comprising subjecting a nucleic acid to a heat stable nuclease which remains active after heating at 100° C. for 30 minutes, produced by Trichoderma or Fusarium.

2. The method of claim 1 wherein the nucleic acid is decomposed at a temperature in the range of about 35° C. to about 100° C.

3. The method of claim 2 wherein the nucleic acid is decomposed at a temperature in the range of about 45° C. to about 100° C.

4. The method of claim 3 wherein the nucleic acid is decomposed at a temperature in the range of about 60° C. to about 100° C.

* * * * *